United States Patent [19]

Suzukamo et al.

[11] Patent Number: 4,723,035
[45] Date of Patent: Feb. 2, 1988

[54] METHOD FOR RACEMIZATION OF CHRYSANTHEMIC ACID OR ITS ESTER

[75] Inventors: Gohfu Suzukamo, Osaka; Masami Fukao, Shiga, both of Japan

[73] Assignee: Sumitomo Chemical Company, Limited, Osaka, Japan

[21] Appl. No.: 10,416

[22] Filed: Feb. 3, 1987

[30] Foreign Application Priority Data

Feb. 27, 1986 [JP] Japan .................................. 61-43442

[51] Int. Cl.$^4$ .............................................. C07B 55/00
[52] U.S. Cl. .................................... 560/124; 562/401; 562/506
[58] Field of Search ................. 562/401, 506; 560/124

[56] References Cited

U.S. PATENT DOCUMENTS

| | | | |
|---|---|---|---|
| 3,666,798 | 5/1972 | Matsui et al. | 562/401 |
| 3,786,070 | 1/1974 | Martel et al. | 562/401 |
| 3,989,750 | 11/1976 | Nagase et al. | 260/544 L |
| 4,182,906 | 1/1980 | Suzukamo et al. | 562/506 |
| 4,473,703 | 9/1984 | Suzukamo et al. | 560/124 |
| 4,485,257 | 11/1984 | Suzukamo et al. | 562/401 |

FOREIGN PATENT DOCUMENTS

0155765 9/1985 European Pat. Off. .
0165070 12/1985 European Pat. Off. .

*Primary Examiner*—Werren B. Lone
*Assistant Examiner*—Vera C. Clarke
*Attorney, Agent, or Firm*—Birch, Stewart, Kolasch & Birch

[57] ABSTRACT

Racemization of optically active, particularly the (−)-form of chrysanthemic acid or its ester of the formula:

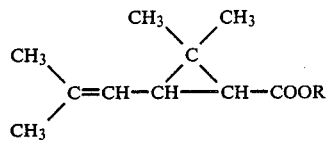

wherein R is, for example, hydrogen or an alkyl group, is effected by contacting it with boron tribromide or aluminum tribromide in the presence of an azo compound. This racemization procedure is useful from a commerical point of view.

10 Claims, No Drawings

METHOD FOR RACEMIZATION OF CHRYSANTHEMIC ACID OR ITS ESTER

The present invention relates to a method for the racemization of chrysanthemic acid or its ester. More particularly, the present invention relates to a method for racemization of optically active chrysanthemic acid or its ester of the formula:

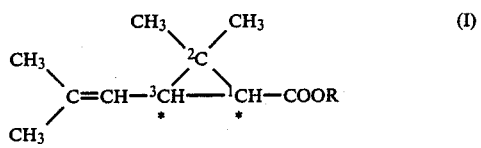

wherein R is hydrogen; an alkyl group which may be substituted with a cycloalkyl group or with an aryl group, the alkyl group having a total number of carbon atoms of from 1 to 20 including the substituent; or a cycloalkyl group which may be substituted with an alkyl or with an alkoxy group, the cycloalkyl group having a total number of carbon atoms of from 5 to 20 including the substituent, which comprises contacting the acid or its ester with a boron bromide compound or an aluminium bromide compound in the presence of an azo compound.

Chrysanthemic acid, i.e. 2,2-dimethyl-3-(2-methyl-1-propenyl)cyclopropane-1-carboxylic acid, constitutes an acid component of esters well-known as so-called pyrethroidal insecticides, such as pyrethrin, allethrin, phthalthrin, etc., which are utilized as low mammalian toxic, quickly effective insecticides, and is useful as intermediates of these esters.

Chrysanthemic acid has four isomers, that is, two geometrical isomers, i.e. cis and trans forms, which respectively have two optical isomers, i.e. (+) and (−) forms. It has been known that, in general, among the isomers the esters composed of the trans-form acid exhibit stronger insecticidal activity than those composed of the corresponding cis-form acid. Furthermore, the esters composed of (+)-form acid exhibit exceedingly higher activity than those composed of the corresponding (−)-isomer.

In general, chrysanthemic acid is industrially produced as a mixture of cis and trans forms, each of which is in the form of racemic mixture, namely, as (±)-form. Optical resolution of the thus-synthesized acid by means of an optically active organic base is conducted to obtain the (+)-form acid which is utilized for the preparation of insecticidal compounds with a high activity. The remaining (−)-isomer after the optical resolution is of little use, since the esters composed thereof are almost inactive. Accordingly, there is a problem to be solved in the production of the (+)-form acid, particularly on a commercial scale, that the (−)-form acid should be racemized at a high efficiency, so as to be utilized again as the material for the optical resolution mentioned above.

Racemization of optically active chrysanthemic acid is difficult, since it possesses two asymmetric carbon atoms exhibited by * marks, as shown above, at the 1- and 3-positions.

Some methods for racemization have so far been studied. The methods known are a method in which (−)-trans-chrysanthemic acid is oxydized at its $C_3$-substituted isobutenyl group to convert to a ketoalcohol group, and the acid group at the $C_1$-position is converted to a lower alkyl ester, which is then subjected to a reaction with an alkali metal alcoholate in a solvent (U.S. Pat. No. 3,282,984); a method in which (−)-trans-chrysanthemic acid is irradiated with ultraviolet rays in the presence of a photosensitizer (U.S. Pat. No. 3,657,086); a method in which optically active chrysanthemic acid is converted to the corresponding acid halide and then is brought into contact with a Lewis acid (U.S. Pat. Nos. 3,989,750 and 4,182,906); and a method in which optically active chrysanthemic acid is converted to acid anhydride and then is brought into contact with iodine (U.S. Pat. No. 4,485,257).

After an extensive study, the present inventors have now found that optically active chrysanthemic acid or its ester of the formula (I) is able to racemize conveniently and in high yield by a treatment with a boron bromide compound or an aluminium bromide compound in the presence of an azo compound. This invention is established on the basis of such finding.

According to the present invention, the optically active chrysanthemic acid or its ester is able to racemize readily and in high yield and the method of the present invention is very convenient for racemization, and particularly in a commercial scale. Moreover, the present invention enables direct utilization, with high efficiency, of (−)-chrysanthemic acid or its ester, which is separated off in the procedures of optical resolution.

The presence of the azo compound reduces the amount of the bromide to be employed and shortens the period of time for racemization. Furthermore, various commercial applications are possible because the azo compound is not so self induction-decomposed that it is easily handled.

The racemization method always gives a trans-rich reaction product regardless of the isomeric composition of the starting material. Since insecticidal activity of pyrethroidal esters in the trans form is generally higher than that of the corresponding esters in the cis form, the above characteristic feature of the racemization method has a great advantage. Thus, the racemization method may be also applied to the conversion of the racemic cis isomer or of a mixture of the racemic cis and trans isomers of the acid or its ester to the corresponding racemic trans-rich isomer.

The method of the present invention will more fully be described hereinafter.

In the present invention, any of the four optical isomers of chrysanthemic acid or its ester is able to be used alone or in mixtures of isomers of the starting material. Namely, the starting material having any degree of optical purity is employed. Needless to say, however, it is preferred to use, as the starting material, (−)-form or rich in (−)-form.

As the chrysanthemic acid ester, mention may be made of, for example, methyl chrysanthemate, ethyl chrysanthemate, propyl chrysanthemate, butyl chrysanthemate, cyclohexyl chrysanthemate, cyclohexylmethyl chrysanthemate and benzyl chrysanthemate.

Boron bromide and aluminium bromide to be used in the present process are, for example, boron tribromide and aluminium tribromide. They are used in such an amount as 1/1000–¼ mol, preferably, 1/200–⅛ mol per mol of chrysanthemic acid or ester thereof.

Azo compounds to be employed include azonitriles such as azobisisobutylonitrile, 2,2'-azobis-(2,4-dimethylvaleronitrile), 1,1'-azobis(cyclohexane-1-carbonitrile), 4,4'-azobis-4-cyanopentanoic acid, 2-phenylazo-2,4- dimethyl-4-methoxyvaleronitrile and 2-cyano-2-propylazoform; azo-esters such as azobisisobutanol diacetate, methyl azobisisobutyrate and ethyl azobisisobutyrate and alkylazo compounds such as azo-t-butane. Azo-nitrile and azo-esters are preferable.

The azo compound is used, in general, in such an amount as from 1/10 to 5 mole, preferably ⅕ to 2 mol, based upon a mole of the boron bromide compound or the aluminium bromide compound employed.

The present racemization reaction is preferably carried out in the presence of an inert solvent. The solvents include saturated aliphatic hydrocarbons, aromatic hydrocarbons and their halide compounds, ethers, etc.

The reaction temperature varies depending on the azo compounds employed. The temperature ranges usually from −20° C. to the boiling point of the chrysanthemic acid or its ester or the boiling point of the solvent when it is employed. The temperature is usually 0° C.–100° C.

The time for reaction varies depending on the amounts of bromide and of an azo compound and reaction temperature, too, but usually ranges from a few minutes to 7 hours.

In carrying out the present racemization reaction in the presence of an azo compound, the following procedure is generally employed. One is the procedure in which the bromide compound is added into a mixture of the starting material to be treated and an azo compound in a solvent, and the other is the procedure in which an azo compound and a bromide compound are added in parallel into the starting material to be treated in a solvent.

The proceeding of the reaction can be checked by measuring the optical rotation, gas-chromatography, etc.

As described above, by the method of the present invention, racemization of the (−)-isomer of optically active chrysanthemic acid or its ester is readily and economically accomplished on a commercial scale. The thus racemized product may be subjected to optical resolution procedures to obtain the useful (+)-isomer of chrysanthemic acid or its ester.

Moreover, the racemization method of the present invention can be also applied to conversion of the racemic cis isomer or of a mixture of the racemic cis and trans isomers of the chrysanthemic acid or its ester to the corresponding racemic trans-rich isomer which is more useful.

The method of the present invention will be described further in the following examples.

EXAMPLE 1

In a 50 ml flask, there were charged (−)-cis-chrysanthemic acid (1.79 g), n-heptane (20 ml), and azobisisobutylonitrile (50 mg) under a nitrogen atmosphere. A solution of boron tribromide (87 mg) in n-heptane was added with stirring for 30 minutes at 80° C.

After the reaction, dil. hydrochloric acid was added to the reaction mixture with stirring to decompose the catalyst. The separated organic layer was extracted with a 10% aqueous sodium hydroxide solution (4.8 g). The aqueous layer was acidified with diluted hydrochloric acid and extracted twice with toluene. The toluene layer was washed with water and dried over sodium sulfate. The solvent was evaporated and the residue was distilled (b.p. 110°–119° C./2.5 mmHg) to obtain 1.61 g of distillate.

The IR spectrum of the product was identical with that of chrysanthemic acid. Gas chromatography assay after conversion to (+)-2-octyl ester gave the following result; (+)-cis, 3.7%; (−)-cis, 6.6%; (+)-trans, 44.6%; (−)-trans, 45.1%.

EXAMPLE 2

In a 50 ml flask, there were charged chrysanthemic acid (composition: (+)-cis, 1.8%; (−)-cis, 18.3%; (+)-trans, 11.2%; (−)-trans; 68.7%) (1.80 g), benzene (8 ml), and azobisisobutylonitrile (58 mg) under a nitrogen atmosphere. A solution of boron tribromide (187 mg) in benzene was added with stirring for 30 minutes at 80° C.

After the reaction, the reaction mixture was treated by the same method as described in EXAMPLE 1 to obtain chrysanthemic acid (1.53 g). Gas chromatography assay after conversion to (+)-2-octyl ester gave the following result: (+)-cis, 3.1%; (−)-cis, 3.4%; (+)-trans, 44.5%; (−)-trans, 49.0%.

EXAMPLE 3

In a 50 ml flask, there were charged chrysanthemic acid (composition: (+)-cis, 1.8%; (−)-cis, 18.3%; (+)-trans, 11.2%; (−)-trans, 68.7%) (3.18 g), dioxane (15 ml), and azobisisobutylonitrile (76 mg) under a nitrogen atmosphere. A solution of aluminium tribromide (260 mg) in toluene was added with stirring for 30 minutes at 80° C.

After the reaction, the reaction mixture was treated by the same method as described in EXAMPLE 1 to obtain chrysanthemic acid (2.73 g). Gas chromatography assay after conversion to (+)-2-octyl ester gave the following result: (+)-cis, 3.2%; (−)-cis, 3.5%; (+)-trans, 41.9%; (−)-trans, 51.4%.

EXAMPLE 4

In a 50 ml flask, there was charged ethyl chrysanthemate (composition: (+)-cis, 2.5%; (−)-cis, 14.8%; (+)-trans, 11.9%; (−)-trans; 70.9%) (4.43 g), benzene (20 ml), and azobisisobutylonitrile (150 mg) under a nitrogen atomsphere. A solution of aluminium tribromide (370 mg) in benzene was added with stirring for 30 minutes at 80° C.

After the reaction, icewater was added to the reaction mixture with stirring to decompose the catalyst. A separated organic layer was concentrated under reduced pressure. To the residue was added a 10% aqueous sodium hydroxide solution (20 g) and the mixture was refluxed for 3 hours. The aqueous layer was washed with toluene. The aqueous layer was acidified with diluted hydrochloric acid and extracted with toluene. The toluene layer was washed with water and dried over sodium sulfate. The solvent was evaporated and the residue was distilled (b.p. 110°–119° C./2.5 mmHg) to obtain 3.34 g of distillate.

The IR spectrum of the product was identical with that of chrysanthemic acid. Gas chromatography assay after conversion to (+)-2-octyl ester gave the following result: (+)-cis, 3.5%; (−)-cis, 3.5%; (+)-trans, 43.0%; (−)-trans, 50.5%.

EXAMPLE 5

In a 50 ml flask, there were charged (−)-cis-chrysanthemic acid (1.15 g), dioxane (15 ml), and methyl azobisisobutylate (45 mg) under a nitrogen atmosphere. A solution of boron tribromide (60 mg) in toluene was added with stirring for 30 minutes at 80° C.

After the reaction, the reaction mixture was treated by the same method as described in EXAMPLE 1 to obtain chrysanthemic acid (1.01 g). Gas chromatography assay after conversion to (+)-2-octyl ester gave the following result: (+)-cis, 3.8%; (−)-cis, 8.1%; (+)-trans, 44.0%; (−)-trans, 44.1%.

EXAMPLE 6

In a 35 ml flask, there were charged cis-chrysanthemic acid (1.68 g), benzene (16.8 ml), and azobisisobutylonitrile (11.5 mg) under a nitrogen atmosphere. A solution of boron tribromide (12.5 mg) in benzene was added with stirring for 10 minutes at 60° C. and the reaction mixture was stirred at the same temperature for 1 hour.

After the reaction, diluted hydrochloric acid was added to the reaction mixture with stirring to decompose the catalyst. Gas chromatographic analysis showed that this product contained 1.63 g of chrysanthemic acid (cis, 6.0%; trans, 94.0%).

EXAMPLE 7

In a 35 ml flask, there were charged cis-chrysanthemic acid (1.6 g), dioxane (20 ml), and methyl azobisisobutylate (63 mg) under a nitrogen atmosphere. A solution of boron tribromide (85 mg) in toluene was added with stirring for 30 minutes at 80° C.

After the reaction, the reaction mixture was treated by the same method as described in EXAMPLE 1 to obtain chrysanthemic acid (1.4 g). Gas chromatography assay gave the result as follows: cis, 10.9%; trans, 89.1%.

EXAMPLE 8

In a 50 ml flask, there were charged ethyl chrysanthemate (composition: cis, 35%; trans, 65%) (4.43 g), benzene (20 ml), and azobisisobutylonitrile (150 mg) under a nitrogen atmosphere. A solution of aluminium tribromide (370 mg) in benzene was added with stirring for 30 minutes at 80° C.

After the reaction, icewater was added to the reaction mixture with stirring to decompose the catalyst. The separated organic layer was concentrated under reduced pressure. To the residue was added a 10% aqueous sodium hydroxide solution (20 g) and the mixture was heated under refluxing for 3 hours. The aqueous layer was washed with toluene. The aqueous layer was acidified with diluted hydrochloric acid and extracted with toluene. The toluene layer was washed with water and dried over sodium sulfate. The solvent was evaporated and the residue was distilled (b.p. 110°–119° C./2.5 mmHg) to obtain 3.35 g of distillate.

The IR spectrum of the product was identical with that of chrysanthemic acid. Gas chromatography assay gave the result as follows: cis, 7.0%; trans, 93.0%.

We claim:

1. A method for racemization of optically active chrysanthemic acid acid or its ester of the formula:

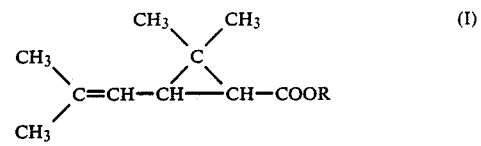

wherein R is hydrogen; an alkyl group which may be substituted with a cycloalkyl group or with an aryl group, said alkyl group having a total number of carbon atoms of from 1 to 20 including the substituent; or a cycloalkyl group which may be substituted with an alkyl or with an alkoxy group, said cycloalkyl group having a total number of carbon atoms of from 5 to 20 including the substituent, which comprises contacting the acid or its ester described above with a boron bromide compound or an aluminium bromide compound in the presence of an azo compound.

2. A method for the conversion of racemic cis isomer or of a mixture of the racemic cis and trans isomers of chrysanthemic acid or its ester of formula:

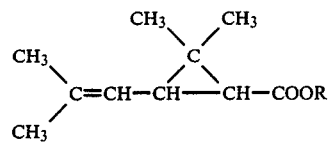

wherein R is hydrogen; an alkyl group which may be substituted with a cycloalkyl group or with an aryl group, said alkyl group having a total number of carbon atoms of from 1 to 20 including the substituent; or a cycloalkyl group which may be substituted with an alkyl or with an alkoxy group, said cycloalkyl group having a total number of carbon atoms of from 5 to 20 including the substituent, to the corresponding racemic trans-rich isomer, which comprises contacting the acid or its ester described above with a boron bromide compound or an aluminium bromide compound in the presence of an azo compound.

3. The method according to claim 1 or 2 wherein the boron bromide compound is boron tribromide.

4. The method according to claim 1 or 2, wherein the aluminium bromide compound is aluminium tribromide.

5. The method according to claim 1 or 2, wherein the azo compound is at least one selected from the group consisting of azonitriles, azoesters and alkylazo compounds.

6. The method according to claim 5, wherein the azo compound is a member selected from the group consisting of azobisisobutylonitrile, 2,2′-azobis-(2,4-dimethylvaleronitrile), 1,1′-azobis(cyclohexane-1 carbonitrile), 4,4′-azobis-4-cyanopentanoic acid, 2-phenylazo-2,4-dimethyl-4-methoxyvaleronitrile, 2-cyano-2-propylazoform, azobisisobutanol diacetate, methyl azobisisobutyrate, ethyl azobisisobutyrate, and azo-t-butane.

7. The method according to claim 1, wherein the azo compound is present in an amount of 1/10 to 5 mole per mole of the boron bromide compound or the aluminum bromide compound.

8. The method according to claim 1, which is carried out in the presence of an inert solvent.

9. The method according to claim 8, wherein the solvent is a member selected from the group consisting of saturated aliphatic hydrocarbons, aromatic hydrocarbons, halide-substituted aromatic hydrocarbons, and ethers.

10. The method according to claim 8, wherein the reaction temperature is from 0° C. to 100° C.

* * * * *